(12) United States Patent
Ghosh (10) Patent No.: US 9,278,219 B2
(45) Date of Patent: Mar. 8, 2016

(54) CLOSED LOOP OPTIMIZATION OF CONTROL PARAMETERS DURING CARDIAC PACING

(71) Applicant: MEDTRONIC, INC., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/833,882

(22) Filed: Mar. 15, 2013

(65) Prior Publication Data
US 2014/0277233 A1    Sep. 18, 2014

(51) Int. Cl.
*A61N 1/36* (2006.01)
*A61N 1/368* (2006.01)
*A61N 1/362* (2006.01)

(52) U.S. Cl.
CPC ............ *A61N 1/3682* (2013.01); *A61N 1/3627* (2013.01); *A61N 1/3684* (2013.01)

(58) Field of Classification Search
USPC .......................................................... 607/17
See application file for complete search history.

(56) References Cited

U.S. PATENT DOCUMENTS

| | | | |
|---|---|---|---|
| 4,233,987 A | 11/1980 | Feingold | |
| 4,428,378 A | 1/1984 | Anderson et al. | |
| 4,497,326 A | 2/1985 | Curry | |
| 4,566,456 A | 1/1986 | Koning et al. | |
| 4,674,511 A | 6/1987 | Cartmell | |
| 5,052,388 A | 10/1991 | Sivula et al. | |
| 5,054,496 A | 10/1991 | Wen et al. | |
| 5,311,873 A | 5/1994 | Savard et al. | |
| 5,443,492 A | 8/1995 | Stokes et al. | |
| 5,628,778 A | 5/1997 | Kruse et al. | |
| 5,671,752 A | 9/1997 | Sinderby et al. | |

(Continued)

FOREIGN PATENT DOCUMENTS

| | | |
|---|---|---|
| EP | 1 072 284 A2 | 1/2001 |
| EP | 1 504 713 A1 | 2/2005 |

(Continued)

OTHER PUBLICATIONS

"State-of-the-Art of Current Applications, Guidelines, Ongoing Trials, and Areas of Controversy", Arrhythmia Management Devices, Cardiac Resynchronization Therapy, Frits W. Prinzen, PhD., et al., 2013; 128: 2407-2418.

(Continued)

*Primary Examiner* — Paula J Stice
(74) *Attorney, Agent, or Firm* — Carol F. Barry (57) ABSTRACT

A system and method control a pacing parameter in a closed-loop manner by determining a value of an EGM-based index corresponding an optimal electrical activation condition of a patient's heart and adjusting a pacing therapy to maintain the EGM-based index value. The closed loop control method performed by the system may establish a relationship between an EGM-based index and multiple settings of a pacing control parameter. Values of the EGM-based index are stored with corresponding setting shifts relative to a previously established optimal setting. A processor of an implantable medical device monitors the EGM-based index during cardiac pacing. Responsive to detecting an EGM-based index value corresponding to a non-optimal setting of the control parameter, the processor determines an adjustment of the control parameter from the stored index values and corresponding setting shifts.

14 Claims, 6 Drawing Sheets

(56) References Cited

U.S. PATENT DOCUMENTS

| | | |
|---|---|---|
| 5,683,432 A | 11/1997 | Goedeke |
| 5,810,740 A | 9/1998 | Paisner |
| 5,891,045 A | 4/1999 | Albrecht et al. |
| 5,922,014 A | 7/1999 | Warman et al. |
| 6,055,448 A | 4/2000 | Anderson et al. |
| 6,187,032 B1 | 2/2001 | Ohyu et al. |
| 6,236,883 B1 | 5/2001 | Ciaccio et al. |
| 6,311,089 B1 | 10/2001 | Mann et al. |
| 6,381,493 B1 | 4/2002 | Stadler et al. |
| 6,393,316 B1 | 5/2002 | Gillberg et al. |
| 6,418,346 B1 | 7/2002 | Nelson |
| 6,442,433 B1 | 8/2002 | Linberg |
| 6,473,638 B2 | 10/2002 | Ferek-Petric |
| 6,480,745 B2 | 11/2002 | Nelson |
| 6,507,756 B1 | 1/2003 | Heynen et al. |
| 6,584,343 B1 | 6/2003 | Ransbury et al. |
| 6,599,250 B2 | 7/2003 | Webb |
| 6,640,136 B1 | 10/2003 | Helland et al. |
| 6,772,004 B2 | 8/2004 | Rudy |
| 6,804,555 B2 | 10/2004 | Warkentin |
| 6,856,830 B2 | 2/2005 | He |
| 6,882,882 B2 | 4/2005 | Struble et al. |
| 6,885,889 B2 | 4/2005 | Chinchoy |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,092,759 B2 | 8/2006 | Nehls et al. |
| 7,142,922 B2 | 11/2006 | Spinelli et al. |
| 7,184,835 B2 | 2/2007 | Kramer |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 8,010,194 B2 | 8/2011 | Muller |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong |
| 8,180,428 B2 | 5/2012 | Kaiser et al. |
| 8,195,292 B2 | 6/2012 | Rosenberg et al. |
| 8,214,041 B2 | 7/2012 | Van Gelder |
| 8,265,738 B1 | 9/2012 | Min |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,380,308 B2 | 2/2013 | Rosenberg |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,617,082 B2 | 12/2013 | Zhang et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,805,504 B2 | 8/2014 | Sweeney |
| 2002/0161307 A1 | 10/2002 | Yu et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0122479 A1 | 6/2004 | Spinelli et al. |
| 2004/0172078 A1 | 9/2004 | Chinchoy |
| 2004/0172079 A1* | 9/2004 | Chinchoy ............... 607/17 |
| 2004/0193223 A1 | 9/2004 | Kramer et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0253162 A1 | 11/2006 | Zhang et al. |
| 2007/0142871 A1 | 6/2007 | Libbus et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |

(56) References Cited

U.S. PATENT DOCUMENTS

| | | |
|---|---|---|
| 2010/0113954 A1 | 5/2010 | Zhou |
| 2010/0114229 A1 | 5/2010 | Chinchoy |
| 2010/0121403 A1* | 5/2010 | Schecter et al. ............... 607/27 |
| 2010/0174137 A1 | 7/2010 | Shim |
| 2010/0198292 A1 | 8/2010 | Honeck et al. |
| 2010/0228138 A1 | 9/2010 | Chen |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054560 A1 | 3/2011 | Rosenberg et al. |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0283587 A1 | 11/2012 | Gosh |
| 2012/0284003 A1 | 11/2012 | Gosh et al. |
| 2012/0296387 A1 | 11/2012 | Zhang et al. |
| 2012/0296388 A1 | 11/2012 | Zhang et al. |
| 2012/0302904 A1 | 11/2012 | Lian |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0304407 A1 | 11/2013 | George et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032172 A1 | 1/2015 | Ghosh |
| 2015/0032173 A1 | 1/2015 | Ghosh |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |

FOREIGN PATENT DOCUMENTS

| | | |
|---|---|---|
| EP | 2 016 976 A1 | 1/2009 |
| EP | 2 391 270 A1 | 7/2011 |
| EP | 1925337 B1 | 3/2012 |
| EP | 2 436 309 A2 | 4/2012 |
| EP | 2 435 132 B1 | 8/2013 |
| WO | WO 98/26712 | 6/1998 |
| WO | WO 00/45700 A1 | 8/2000 |
| WO | WO 01/67950 A1 | 9/2001 |
| WO | WO 2005/056108 A2 | 6/2005 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/013994 A3 | 4/2007 |
| WO | WO 2007/139456 A1 | 12/2007 |
| WO | WO 2008/151077 A2 | 12/2008 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

"Electrophysiological Substrate and Intraventricular LV dyssynchrony in Non-ischemic Heart Failure Patients Undergoing Cardiac Resynchronization Therapy", by Subham Ghosh et al., The Heart Rhythm Society, May 2011; 8 (5): 692-699.

"Electrical and Mechanical Ventricular Activation During Left Bundle Branch Block and Resynchronization", by Marc Strik, et al., J. of Cardiovasc. Trans. Res. (2012) 5:117-126.

"Analysis of Ventricular Activation Using Surface Electrocardiography to Predict Left Ventricular Reverse Volumetric Remodeling During Cardiac Resynchronization Therapy", by Michael O. Sweeney, M.D., et al., Circulation Journal of the American Heart Association, Jan. 25, 2010, 121; pp. 626-634.

"Mathematical Modeling and Simulation of Ventricular Activation Sequences: Implications for Cardiac Resynchronization Therapy", by Mark Potse, J. Cardiovasc Transl Res., 2012 Apr, 5(2): 146-158.

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

"CardioGuide System Enables Real-Time Navigation of Left Ventricular Leads During Medtronic CRT Implants," Press Release, Apr. 9, 2013, Medtronic, Inc., 2 pgs.

Cuculich, P.S., et al., "The Electrophysiological Cardiac Ventricular Substrate in Patients After Myocardial Infection" *J. Am. Coll. Cardiol.* 2011; 58:1893-1902.

Czerwinska et al., "Method of Segmentation of Thorax Organs Images Applied to Modeling the Cardiac Electrical Field," *Engineering in Medicine and Biology Society*, Proceedings of the 22nd Annual International Conference of the IEEE, vol. 1, 23, Jul. 23, 2000; pp. 402-405.

Dawoud, F. et al., "Inverse Electrocardiographic Imaging to Assess Electrical Dyssynchrony in Cardiac Resynchronization Therapy Patients," *Computing in Cardiology*, 2012; 39:993-996.

(56) References Cited

OTHER PUBLICATIONS

Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.

Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.

Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar., 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," *Heart Rhythm*, Sep. 2011; 8(9):1469-1475.

"Heart Failure Management" datasheet [online]. Medtronic, Minneapolis, Minnesota, [Last updated on Jun. 3, 2013].Retrieved from the Internet: www.medtronic.com; 9 pages.

Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of ST Segment Changes in Acute Myocardial Infarction," *Circulation*, 1993; 87: 773-782.

Medtronic Vitatron CARELINK ENCORE® Programmer Model 29901 Reference Manual, 2013, Medtronic, Inc., Minneapolis, MN.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.

Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms : a simulation study," *Circulation Research*, 1989, 64:449-462.

Turner et al, "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

| RHYTHM | AV DELAY SHIFT (ms) | EGM-BASED INDEX (ms) | RHYTHM | AV DELAY SHIFT (ms) | EGM-BASED INDEX (ms) |
|---|---|---|---|---|---|
| SAV-BV 402a | 0 | 50 | PAV-BV 402c | 0 | 50 |
| | -10 | 52 | | -10 | 52 |
| | -20 | 62 | | -20 | 62 |
| | -30 | 70 | | -30 | 70 |
| | -40 | 80 | | -40 | 80 |
| | -50 | 80 | | -50 | 80 |
| | 10 | 48 | | 10 | 48 |
| | 20 | 45 | | 20 | 45 |
| | 30 | 34 | | 30 | 34 |
| | 40 | 30 | | 40 | 30 |
| | 50 | 22 | | 50 | 22 |
| SAV-LV 402b | 0 | 50 | PAV-LV 402d | 0 | 50 |
| | -10 | 52 | | -10 | 52 |
| | -20 | 58 | | -20 | 58 |
| | -30 | 61 | | -30 | 61 |
| | -40 | 64 | | -40 | 64 |
| | -50 | 65 | | -50 | 65 |
| | 10 | 40 | | 10 | 40 |
| | 20 | 35 | | 20 | 35 |
| | 30 | 32 | | 30 | 32 |
| | 40 | 28 | | 40 | 28 |
| | 50 | 22 | | 50 | 22 |

CLOSED LOOP OPTIMIZATION OF CONTROL PARAMETERS DURING CARDIAC PACING

TECHNICAL FIELD

The disclosure relates generally to optimizing control parameters during cardiac pacing therapies and more particularly to optimizing pacing therapy control parameters based on relationships between an index determined from intracardiac electrogram (EGM) signals and ventricular activation.

BACKGROUND

Cardiac resynchronization therapy (CRT) is a treatment for heart failure patients in which one or more heart chambers are electrically stimulated (paced) to restore or improve heart chamber synchrony. Improved heart chamber synchrony is expected to improve hemodynamic performance of the heart, such as assessed by ventricular pressure and the rate of change in ventricular pressure or other hemodynamic parameters, thereby alleviating symptoms of heart failure. Achieving a positive clinical benefit from CRT is dependent on several therapy control parameters, such as the atrio-ventricular (AV) delay and the inter-ventricular (VV) delay. The AV delay controls the timing of ventricular pacing pulses relative to an atrial depolarization, intrinsic or paced. The VV delay controls the timing of a pacing pulse in one ventricle relative to a paced or intrinsic sensed event in the other ventricle.

Numerous methods for selecting optimal AV and VV delays for use in controlling CRT pacing pulses have been proposed. For example, clinicians may select an optimal AV or VV delay using Doppler echocardiography or other imaging modalities to optimize a hemodynamic variable. Such clinical techniques are time-consuming, require an expert technician to perform, and are performed at a discreet time, such as at device implantation or during a clinical visit, without ongoing adjustment to the CRT therapy parameters as the need may arise. Other methods may be based on a hemodynamic sensor signal or a sensor of mechanical heart function. Such methods may require additional sensors and therefore add cost to the overall system. A need remains, therefore, for a device and method that enables closed loop optimization of CRT therapy parameters for restoring ventricular synchrony and alleviating the symptoms of heart failure associated with ventricular dyssynchrony.

SUMMARY

In general, the disclosure is directed towards techniques for controlling a pacing control parameter during a pacing therapy. In particular, a control parameter such as a timing parameter, e.g., an AV delay or a VV delay, is controlled by an implantable medical device processor using a relationship established between an index derived from an EGM signal and pacing control parameter settings corresponding to an optimal electrical activation condition and corresponding to non-optimal electrical activation conditions. An implantable medical device processor may be configured to determine a value of the EGM-based index during an unknown electrical activation condition of a patient's heart and adjust a pacing therapy to maintain the EGM-based index at a value previously established as corresponding to optimal electrical activation synchrony.

In some examples, an optimal control parameter setting is established by a processor determining a ventricular dyssynchrony index from surface ECG electrode signals. Activation times are determined from surface ECG signals that are acquired from multiple surface electrodes. A ventricular dyssynchrony index is determined from the activation times. An optimal setting of the control parameter is determined based on the ECG-based ventricular dyssynchrony index, establishing an optimal electrical activation condition for which the EGM-based index corresponding to the optimal activation condition is determined.

The relationship between an EGM-based index and multiple settings of the control parameter is established by delivering cardiac pacing according to each of a plurality of control parameter settings, including a previously established optimal setting and at least one non-optimal setting different than the optimal setting. The EGM-based index is determined from a EGM signal acquired during each of the settings. Values of the determined index are stored with corresponding parameter setting differences or shifts relative to the optimal setting for each of the multiple settings. The EGM-based index is monitored during cardiac pacing. Responsive to detecting an EGM-based index value corresponding to a non-optimal setting of the control parameter, an adjustment of the control parameter is determined from the stored relationship between the EGM-based index and corresponding setting shifts.

In one example, a method includes establishing a relationship between an EGM-based index and a plurality of settings of a pacing control parameter. Establishing this relationship includes delivering cardiac pacing according to each of a plurality of settings comprising a previously established optimal setting and at least one non-optimal setting different than the optimal setting by a setting shift, determining the EGM-based index from an EGM signal acquired for each of the plurality of settings, and storing values of the determined index with corresponding setting shifts relative to the optimal setting for each of the plurality of settings. The method further includes monitoring the EGM-based index during cardiac pacing, and, responsive to detecting an EGM-based index value corresponding to a non-optimal setting of the control parameter, determining an adjustment of the control parameter from the stored index values and corresponding setting shifts. The control parameter is adjusted by the determined adjustment.

In another example, a system includes a plurality of cardiac electrodes, a cardiac signal generator coupled to the plurality of cardiac electrodes, a sensing module coupled to the plurality of electrodes, and a processor. The cardiac signal generator delivers cardiac pacing according to each of a plurality of settings of a pacing control parameter, the plurality of settings comprising a previously established optimal setting and at least one non-optimal setting different than the optimal setting by a setting shift. The sensing module senses an EGM signal during the cardiac pacing. The processor is configured to establish a relationship between an EGM-based index and the plurality of settings by determining the EGM-based index from the EGM signal acquired for each of the plurality of settings and storing values of the determined index with corresponding setting shifts of each of the plurality of settings relative to the optimal setting. The processor is further configured to monitor the EGM-based index during cardiac pacing; and, responsive to detecting an EGM-based index value corresponding to a non-optimal setting of the control parameter, determine an adjustment of the control parameter from the stored index values and corresponding setting shifts. The processor adjusts the control parameter by the determined adjustment In another example a non-transitory, computer-readable storage medium includes instructions that, when executed, cause a processor to establish a relationship between an EGM-based index and a plurality of settings of a pacing control parameter, monitor the EGM-based index during cardiac pacing, responsive to detecting an EGM-based index value corresponding to a non-optimal setting of the control parameter, determine an adjustment of the control parameter from the stored index values and corresponding setting shifts, and adjust the control parameter by the determined adjustment.

The details of one or more aspects of the disclosure are set forth in the accompanying drawings and the description below. Other features, objects, and advantages will be apparent from the description and drawings, and from the claims.

DETAILED DESCRIPTION

Fundamentally, CRT alters electrical activation of the ventricles, improving spatial synchronization of electrical conduction in hearts with electrical conduction disorders such as left bundle branch block, right bundle branch block or other disorders. Optimal electrical activation of the heart may therefore be important for CRT efficacy. Optimal electrical activation can depend on a number of factors including the location of the pacing electrodes and pacing timing parameters such as AV delay and VV delay. Techniques disclosed herein enable an IMD to perform closed loop optimization of electrical activation of the heart.

Figure 1:
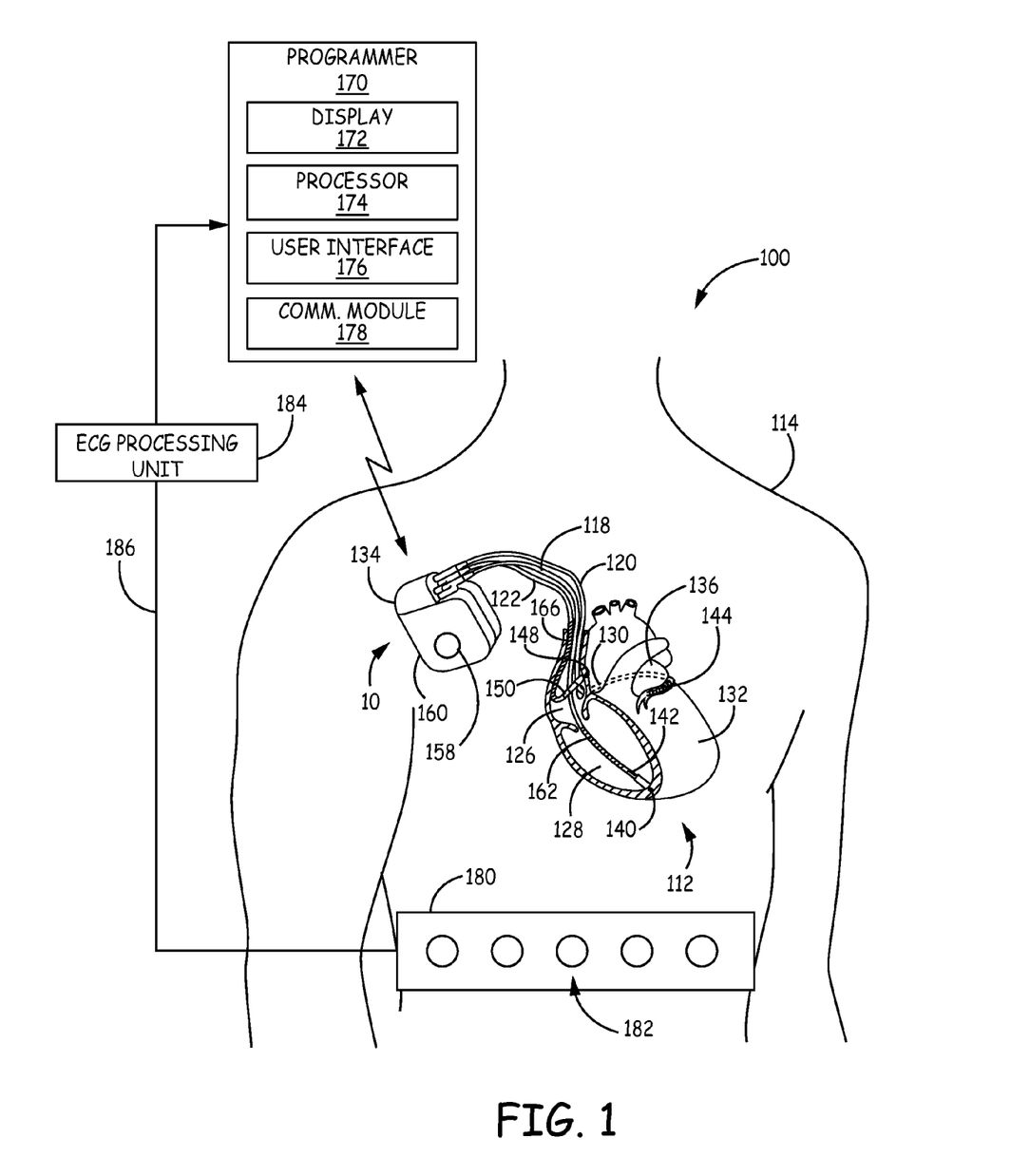
FIG. 1 is a schematic diagram of one embodiment of an implantable medical device (IMD) system in which techniques disclosed herein may be implemented.

FIG. 1 is a schematic diagram of one embodiment of an implantable medical device (IMD) system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10. Housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT by delivering pacing pulses in one or both ventricles 128 and 132 for controlling and improving ventricular synchrony. LV pacing may be delivered using a selected pacing vector that utilizes at least one electrode 144 on multipolar LV lead 120. RV pacing is delivered using RV tip electrode 140 and ring electrode 142. CRT may be delivered by pacing in a single ventricular chamber (LV or RV) or both chambers (biventricular pacing) depending on patient need. The methods described herein are implemented in a dual or multi-chamber pacemaker or ICD delivering pacing pulses to the right and/or left ventricles using programmable pacing pulse timing parameters and selected pacing vectors.

In some embodiments, IMD 10 is configured to provide "adaptive CRT" which automatically switches between biventricular pacing and LV-only pacing in response to changes in the patient's intrinsic AV conduction. When AV conduction is impaired or blocked, or more generally when AV conduction time is slowed, biventricular pacing is delivered. When normal AV conduction returns, LV-only pacing is delivered. In this way, RV pacing is delivered only when needed based on the patient's own AV conduction status, which may fluctuate over time.

While a multi-chamber ICD is shown in FIG. 1, it is recognized that techniques disclosed herein may be implemented in a single chamber, dual chamber or multi-chamber pacemaker, with or without anti-arrhythmia therapies such as cardioversion and defibrillation shock capabilities. For example, techniques disclosed herein for closed-loop optimization of a CRT control parameter may be used to optimize the AV delay applied between an atrial event, sensed or paced, and a ventricular pacing pulse delivered in one ventricle (RV or LV only) or biventricular pacing pulses (RV and LV).

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 can initiate a CRT optimization procedure performed by IMD 10 automatically or semi-automatically, to establish data for closed-loop optimization of CRT control parameters. As will be described herein, an EGM-based index value, corresponding to varying states of ventricular activation synchrony as assessed from surface ECG signals, is determined from an EGM signal sensed using selected cardiac electrodes 140, 142, 144, 162, 166 or housing electrode 158. The EGM-based index values are determined during CRT as it is delivered using varying parameter settings to establish EGM-based index data corresponding to differing states of ventricular dyssynchrony. The EGM-based index data is used for optimizing the control parameter in a closed-loop manner by IMD 10. This EGM-based index, derived from the EGM signal, is also referred to herein as an "EGM-based dyssynchrony index" because its relationship to CRT control parameter settings associated with optimal ventricular electrical synchrony and with non-optimal ventricular electrical synchrony is established. Knowledge of a patient-specific optimal electrical synchrony condition is established using surface ECG electrode signals, and the EGM-based index is recorded for an optimal CRT parameter setting, such as AV delay, as well as multiple non-optimal settings.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS, for example as described in U.S. Pat. No. 5,683,432 (Goedeke, et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems may be configured to utilize the presently disclosed techniques to enable a clinician to review CRT therapy parameters and authorize programming of IMD 10. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety.

System 100 further includes an array of surface electrodes 182, which may be carried by a belt or strap 180 adapted to be wrapped around the torso of patient 114 to position electrodes 182 in the vicinity of heart 112. Strap 180 is shown inferior to heart 112 in FIG. 1, but it is understood that belt 180 may be positioned in a relatively more superior position to surround heart 112 such that electrodes 180 are positioned nearer to heart 112. Electrodes 182 are used to acquire surface signals from heart 112 during a CRT optimization session. A CRT control parameter, such as the AV delay and/or VV delay may be optimized by adjusting the parameter until the surface ECG-based determinations of ventricular activation indicate optimally synchronized ventricular activation. EGM data is then generated by IMD 10 at the optimized parameter setting and multiple increments/decrements from the optimal delay setting to establish EGM-based dyssynchrony index data and its relationship to increments or decrements from optimal control parameter settings, specific to the patient. The EGM-based data is used by IMD 10 to adjust the control parameter in a closed loop to maintain optimized ventricular activation.

In one example illustrated in FIG. 1, strap 180 is wrapped around the torso of patient 114 such that the electrodes 182 surround heart 112. Electrodes 182 may be positioned around the circumference of patient 114, including the posterior, lateral, and anterior surfaces of the torso of patient 114. In other examples, electrodes 182 may be positioned on any one or more of the posterior, lateral, and anterior surfaces of the torso. Electrodes 182 may be electrically connected to an ECG processing unit 184 via a wired connection 186. Some configurations may use a wireless connection to transmit the signals sensed by electrodes 182 to ECG processing unit 184, e.g., as channels of data.

Although in the example of FIG. 1, strap 180 is shown carrying surface electrodes 182, in other examples any of a variety of mechanisms, e.g., tape or adhesives, may be employed to aid in the spacing and placement of electrodes 182. In some examples, strap 180 may include an elastic band, strip of tape, or cloth. In some examples, electrodes 182 may be placed individually on the torso of patient 114.

Electrodes 182 may surround heart 112 of patient 114 and record the electrical signals associated with the depolarization and repolarization of heart 112. Each of electrodes 182 may be used in a unipolar configuration to sense the surface potentials that reflect the cardiac signals. ECG processing unit 184 may also be coupled to a return or indifferent electrode (not shown) which may be used in combination with each of electrodes 182 for unipolar sensing. In some examples, there may be 12 to 16 electrodes 182 spatially distributed around the torso of patient 114. Other configurations may have more or fewer electrodes 182.

ECG processing unit 184 may record and analyze the surface potential signals, referred to generally herein as "ECG" signals, sensed by electrodes 182. Processing unit 184 may be configured to provide an output to a user indicating electrical dyssynchrony of heart 112. The user may make a diagnosis, prescribe CRT, position therapy devices, e.g., leads, or adjust or select treatment parameters based on the indicated electrical dyssynchrony.

ECG processing unit 184 may compute activation times directly from sensed surface potential signals. An activation time for each electrode location (of electrodes 182) may be determined as a time period between two events, such as between the QRS complex onset and the minimum derivative during the QRS signal (i.e., the steepest negative slope of the sensed potential signal) at the respective electrode. Values of one or more indices indicative of the temporal and/or spatial distribution of the activation times may be determined as measures or indicators of electrical dyssynchrony. These indicators of electrical dyssynchrony may be used to evaluate different CRT control parameters and identify an optimal CRT control parameter.

Examples of indices of cardiac electrical dyssynchrony that may be calculated from surface potential signals sensed by electrodes 182 include a standard deviation of the determined activation times, a range of activation times, and a percentage of late activations. All or a subset of the surface electrodes (e.g., only electrodes located on the left anterior, left lateral and left posterior regions of the torso) may be used for calculation or computation of the activation times. The range of activation times may be computed as the difference between the maximum and the minimum cardiac activation times determined from all or a subset of electrodes 182. The percentage of late activations estimates the percentage of electrodes 182 whose associated activation times are greater than a certain percentile, for example the $70^{th}$ percentile, of the QRS complex duration or the determined activation times for electrodes 182. Techniques for determining indices of electrical dyssynchrony based on surface activation times are generally disclosed in commonly-assigned pre-grant U.S. Patent Publication No. 2012/0283587 A1 (Ghosh, et al.) hereby incorporated herein by reference in its entirety. Indices of electrical dyssynchrony derived from external surface ECG leads are generally described. CRT optimization based on such indices derived from surface ECG leads can be performed at implant or at patient follow-up visits. Techniques disclosed herein, however, enable tuning of pacing timing parameters in an ongoing closed-loop manner to maintain optimal electrical activation of the ventricles in a patient-specific manner.

One or more indices of ventricular dyssynchrony based on the surface potential signals sensed by electrodes 182 is used to identify an optimal CRT parameter setting, such as an AV or VV delay. A user may program the AV delay into IMD 10 using programmer 170. In some embodiments, ECG processing unit 184 and programmer 170 are in wired or wireless communication or integrated in a common device that enables system 100 to automatically step through multiple CRT parameter settings, record and analyze surface potential signals to obtain one or more ECG-based indices of ventricular dyssynchrony, and identify and program an optimal setting for the CRT parameter based on analysis of ventricular electrical activations determined from surface ECG signals and the synchrony or dyssynchrony thereof.

The strap 180 carrying electrodes 182 is one illustrative embodiment of an apparatus that is useful in recording surface ECG signals from which ventricular activation times can be determined. Other surface cardiac signal recording apparatus may be used for acquiring cardiac signal data from which ventricular activation times can be computed and used in computing an index of ventricular dyssynchrony for establishing an optimal setting of one or more CRT control parameters. Other signal recording apparatus and techniques may include 12-lead ECG electrodes, a vest carrying an array of electrodes, and vectorcardiography.

Once an optimal CRT parameter is established based on optimal synchronization of electrical activation signals of the ventricles derived from surface ECG signals, CRT is delivered by IMD 10 using the optimal parameter setting and multiple non-optimal settings increased or decreased, i.e. shifted, from the optimal setting. IMD 10 acquires EGM signals for the optimal setting and multiple non-optimal settings to establish EGM parameter data for differing states of ventricular activation, i.e. different states of optimal electrical synchrony and non-optimal electrical synchrony corresponding to different increments and/or decrements from the optimal setting of the control parameters. This EGM parameter data is stored by IMD 10 and used in closed-loop CRT control parameter optimization as will be described herein.

Figure 2:
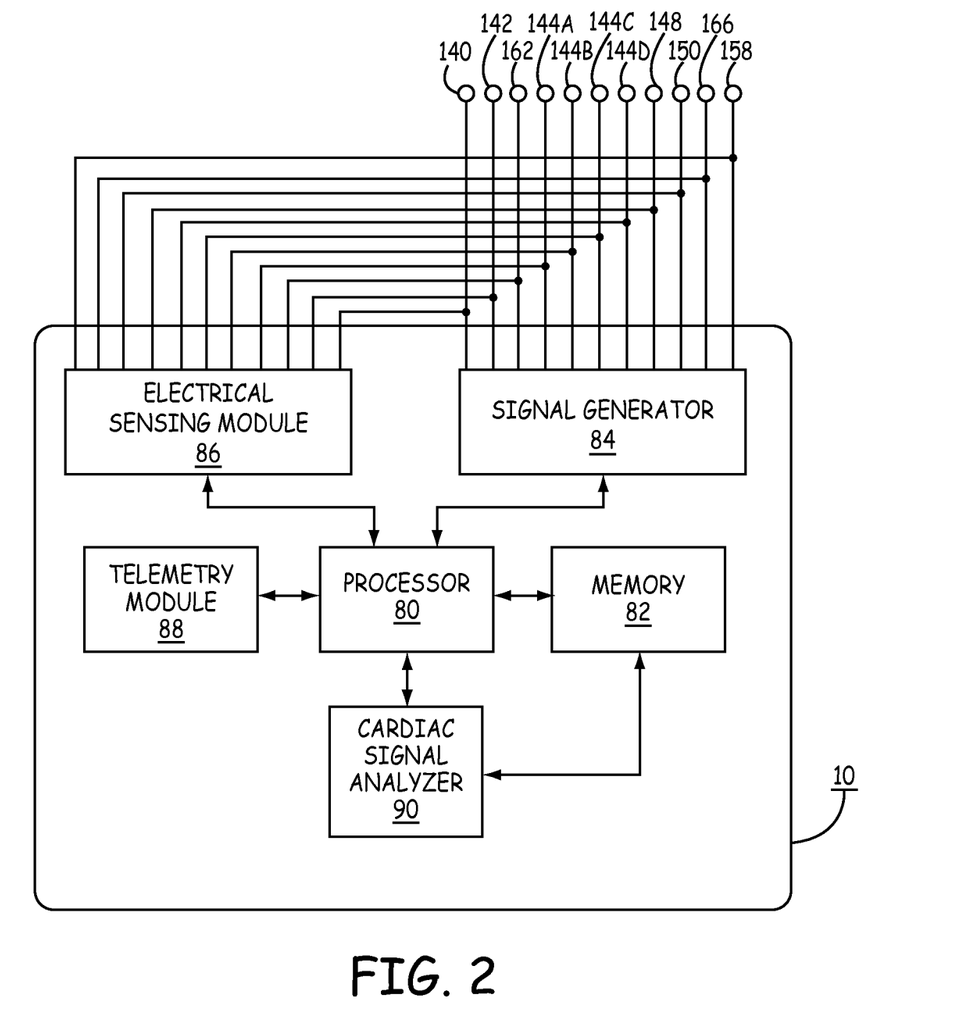
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, also referred to herein as "processor" 80, memory 82, signal generator 84, sensing module 86, and telemetry module 88. IMD 10 further includes cardiac signal analyzer 90.

Memory 82 may include computer-readable instructions that, when executed by processor 80, cause IMD 10 and processor 80 to perform various functions attributed throughout this disclosure to IMD 10, processor 80, and cardiac signal analyzer 90. The computer-readable instructions may be encoded within memory 82. Memory 82 may comprise non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory propagating signal.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, cardiac signal analyzer 90 may, at least in part, be stored or encoded as instructions in memory 82 that are executed by processor and control unit 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 delivers cardiac pacing pulses according to AV and/or VV delays during CRT. These delays are set based on an analysis of cardiac signals by analyzer 90 as will be described herein.

Signal generator 84 may include a switch module (not shown) and processor and control 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac electrical signals for sensing cardiac electrical events, e.g. P-waves and R-waves, from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 includes multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112, e.g. ventricular sense events and atrial sense events corresponding to intrinsic depolarization of the respective heart chamber. Sensing module 86 may further include digital signal processing circuitry for providing processor 80 or cardiac signal analyzer 90 with digitized EGM signals.

The occurrence of R-waves in the ventricles, e.g. in the RV, may be used in monitoring intrinsic AV conduction time. In particular, prolongation of the AV conduction time or the detection of AV block based on R-wave sensing during no ventricular pacing (or pacing at an extended AV delay that allows intrinsic conduction to take place) is used to control adaptive CRT in some embodiments. When AV conduction is impaired, signal generator 84 is controlled by processor 80 to deliver biventricular pacing, i.e. pacing pulses are delivered in the RV and the LV using a selected AV delay and a selected VV delay. When AV conduction is intact, signal generator 84 is controlled by processor 80 to deliver LV-only pacing at a selected AV delay to optimally improve ventricular synchrony according to an EGM-based parameter whose relationship to ventricular electrical activation synchrony has been previously established.

As described herein, the AV delay may be optimized uniquely for different heart rhythm states such as rhythm states involving atrial sensing, atrial pacing, LV-only pacing, or biventricular pacing. For example, four distinct atrioventricular rhythm states may be evaluated: 1) atrial-sensed, biventricular paced 2) atrial-paced, biventricular paced 3) atrial-sensed, LV-only paced and 4) atrial-pace, LV-only paced. EGM-based ventricular dyssynchrony data may be established for different rhythm states and used to adjust the AV delay according to the EGM-based data and the current atrial sensing or pacing rhythm state and/or LV-only or biventricular pacing state.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event in another chamber. Memory 82 stores look-up tables and/or equations established for adjusting CRT control parameters such as AV and VV delays as will be described herein. Equations may be stored in the form of coefficient and intercept values defining a relationship between an EGM-based ventricular dyssynchrony parameter and different settings of a control parameter.

Figure 3:
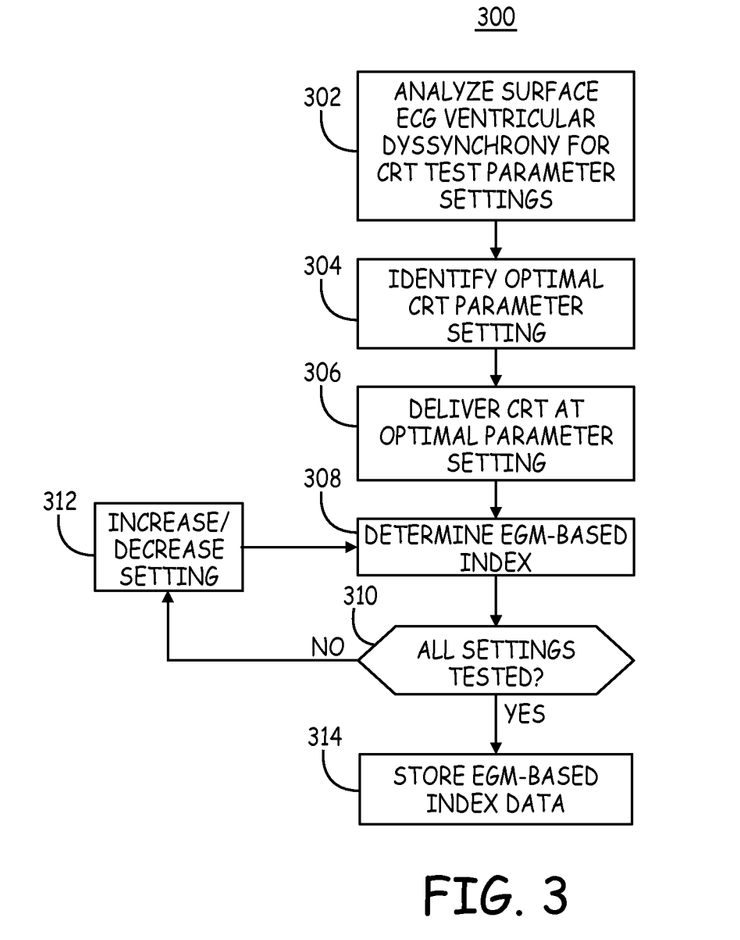
FIG. 3 is a flow chart of a method for generating EGM-based index values according to one embodiment.

FIG. 3 is a flow chart 300 of a method for generating EGM-based ventricular dyssynchrony data for use in closed-loop adjustments of a CRT control parameter according to one embodiment. At block 302, ventricular dyssynchrony is assessed by analyzing activation times determined at multiple surface electrodes as described above and in the incorporated '587 published application. One or more indices of ventricular dyssynchrony are determined for each CRT parameter setting to be tested. Based on the analysis of activation times determined from surface electrodes, an optimal CRT parameter setting is identified at block 304. For example, a CRT control parameter resulting in a minimized activation time range, a minimum activation time standard deviation, and/or a minimized percentage of late activation times may be identified as an optimal CRT parameter.

One or more CRT parameters may be evaluated. Parameters that may be evaluated include AV delay and VV delay. Furthermore, each of these timing parameters may be evaluated during different rhythm conditions or states, e.g. during atrial sensing and during atrial pacing (with ventricular pacing occurring in one or both ventricles). In one embodiment, AV delay is set to multiple settings during an atrial pacing rhythm and during an atrial sensing rhythm to identify an optimal AV delay during atrial sensing (SAV delay) and during atrial pacing (PAV delay).

Additionally, AV delay may be set to multiple settings during pacing in one ventricle, RV-only and/or LV-only, and during biventricular pacing. During biventricular pacing, multiple settings of VV delay may be tested. For example, once an optimal AV delay is identified using a nominal VV delay, multiple VV delay settings may be applied to determine the optimal VV delay according to an ECG-based index of ventricular dyssynchrony.

In some embodiments, multiple pacing vectors may be available. For example, as shown in FIG. 1, a multi-polar CS lead may include multiple electrodes available for pacing the LV. Accordingly, an optimal AV delay resulting in a minimized index of ventricular dyssynchrony based on surface activation time determinations may be identified for each available pacing vector. When a pacing vector is changed, for example due to a change in lead impedance or other condition, the AV or VV delay may be adjusted to an optimal setting identified for the new pacing vector.

Once an optimal setting is established for a CRT parameter block 304, CRT is delivered at the optimal parameter setting(s) at block 306. An EGM signal is acquired by sensing module 86 and provided to cardiac signal analyzer 90. Signal analyzer 90 determines a ventricular dyssynchrony parameter from the EGM signal at block 308.

One or more sensing vectors may be selected from the available cardiac electrodes to provide EGM signals for determining a parameter of the EGM signal during different control parameter settings. In one embodiment, an EGM sensing vector selected for computing an EGM-based parameter for assessing a ventricular electrical dyssynchrony state is from an LV cathode electrode 144 to RV coil electrode 162 (shown in FIG. 1). An index may be computed as the time interval between two fiducial or reference points of the EGM signal. In one embodiment, the EGM-based index is determined as the time interval between a maximum amplitude and the minimum amplitude of an EGM signal during a monitoring window, e.g. a 200 ms window, immediately following a pacing pulse (or after a blanking interval following the pacing pulse). Alternatively, the ventricular dyssynchrony index may be determined as the time interval from a pacing pulse to a maximum amplitude of the EGM signal sensed from the selected sensing vector. The index may be an averaged value of multiple indices obtained from multiple cardiac cycles.

After recording the EGM-based index for the optimal CRT parameter setting at block 308, the parameter setting is increased or decreased at block 312 to a non-optimal setting by a known increment/decrement. The EGM-based index is determined for the new setting by returning to block 308. This process of increasing or decreasing the CRT parameter by known increments/decrements is repeated until an EGM-based index has been recorded for all desired CRT parameter test settings as determined at block 310.

The EGM-based index is stored for each test setting, along with the difference between the test (non-optimal) setting and the optimal setting for the CRT parameter at block 314. In this way, an EGM-based index is characterized for a known optimal ventricular activation condition, i.e. the optimal CRT parameter setting identified in response to surface ECG analysis, and for multiple non-optimal settings. In other words, a relationship is established between the EGM-based index and multiple parameter settings, including the optimal setting and one or more non-optimal settings different than, i.e. shifted from, the optimal setting.

Knowing the value of the EGM-based index during optimized electrical activation of the ventricles, adjustments to the CRT control parameter may be made to return the EGM-based index toward the value associated with electrical activation synchrony in a closed-loop control method. The optimal control parameter setting, such as AV delay, may change with changes in heart rate, activity or other conditions. This variation in an optimal setting occurs when intrinsic AV conduction timing changes. To maintain optimal ventricular activation under changing conditions, the optimal control parameter setting, like the A-V delay, needs to be adjusted so that the relationship of the timing of a CRT ventricular pacing pulse and the timing of intrinsic ventricular conduction remains consistent. However, to determine the intrinsic AV conduction and its changes directly, ventricular pacing needs to be inhibited temporarily, suspending CRT therapy. Even short disruptions in CRT therapy may be undesirable in some patients. By monitoring the EGM-based index and its changes during CRT pacing, it is possible to detect a need to adjust a timing control parameter without temporary suspension of CRT therapy.

Adjustments to control parameters, like the A-V delay, may be made based on the stored patient-specific relationship of the EGM-based index to increments and decrements of the control parameters. In this way, the EGM-based index can be restored to the value associated with optimal electrical activation synchrony and maintained at this value regardless of heart rate, intrinsic conduction changes or other changing conditions.

Figure 4:
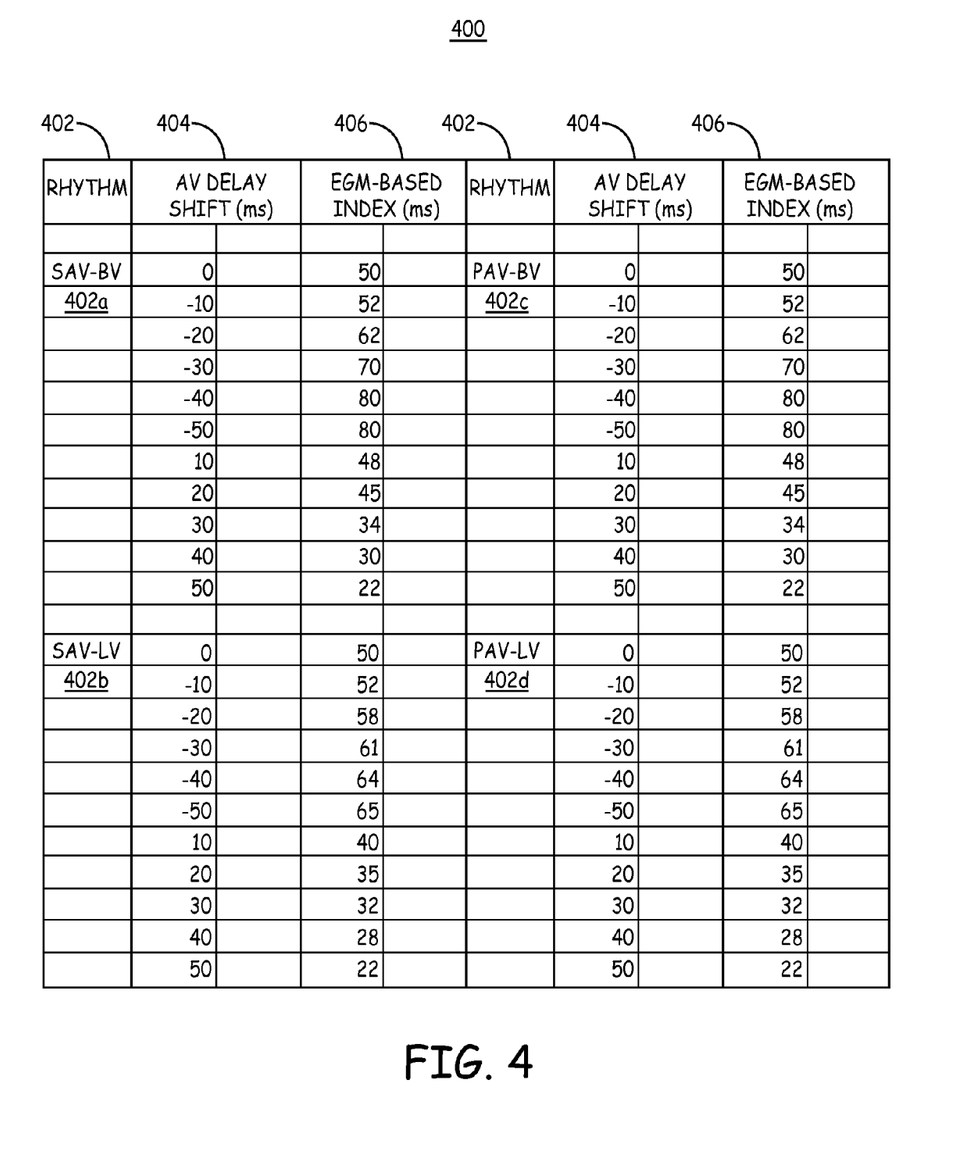
FIG. 4 depicts look-up table data that may be generated using the method shown in FIG. 3 according to one embodiment.

FIG. 4 depicts a look-up table 400 that may be generated using the method shown in FIG. 3 according to one embodiment. If AV delay is the CRT parameter being optimized, after setting an optimal AV delay based on a ventricular dyssynchrony index computed from ECG surface potential signals, the IMD 10 may be triggered to establish EGM-based index data, for example by a command received from programmer 170.

The signal generator 84 is controlled to deliver a ventricular pacing pulse to one or both ventricles using the previously established optimal AV delay. In the illustrative example, CRT is delivered during four different rhythm states 402, including single ventricular pacing (LV only) and biventricular pacing (LV and RV) during both atrial sensing and atrial pacing. Ventricular pacing pulses may be delivered simultaneously to the RV and LV during atrial sensing (SAV-BV) 402a and during atrial pacing (PAV-BV) 402c or at a nominal VV interval. For establishing the index data during biventricular pacing, a nominal V-V delay, e.g. 0 ms, or other previously established value may be used. An LV-only pulse is delivered during atrial sensing (SAV-LV) 402b and during atrial pacing (PAV-LV) 402d.

During pacing, the ventricular pacing pulses are delivered at varying AV delays. The cardiac signal analyzer 90 receives a selected EGM signal, e.g. from an LV electrode 144 to RV coil 162 sensing vector or any other available sensing vector, and determines an index from the EGM signal. In one embodiment the EGM-based index is the time interval between a maximum and minimum amplitude in a 200 ms window following the ventricular pacing pulse(s).

The EGM-based index 406 is computed during pacing using the optimal AV delay for each of the rhythm states and stored in the look-up table 400 with an associated 0 ms shift from the optimal AV delay setting. The AV delay shift 404 is the difference between a non-optimal AV delay and the optimal A-V delay. The EGM-based index is computed and stored for multiple increments and decrements relative to the optimal AV delay. For each AV delay setting, the EGM-based index 406 is stored for each corresponding AV delay shift 404 relative to the optimal AV delay. For example, the AV delay may be decreased by decrements of 10 ms to obtain EGM-based index values at AV delay shifts of −10, −20, −30, −40 and −50 ms relative to the optimal AV delay. The AV delay may be additionally increased by increments of 10 ms to obtain EGM-based indexes for each AV delay shift relative to the optimal AV delay of +10, +20, +30, +40 and +50 ms. The size of the AV delay shifts relative to the optimal AV delay and the number of different settings greater and less than the optimal AV delay may vary based on what the optimal delay is, what the intrinsic AV timing interval is for a particular patient, and what range and resolution of settings are available in the IMD.

The shift or difference between the optimal delay and a non-optimal delay is stored in the look up table 400 instead of the actual delay values since the optimal delay resulting in an optimized EGM-based index value will vary with changing heart rate, intrinsic conduction, or other factors. It is the relationship between the EGM-based index and relative shifts (increments or decrements) of the control parameter setting from an optimal setting that is established by collecting the data shown in look up table 400.

The EGM-based index 406 may be recorded in the look up table 400 in IMD memory 82 for each rhythm type 402 for multiple AV delay shifts 404 relative to the optimal AV delay. It is contemplated that EGM-based indexes may be determined for establishing look up table data relating the EGM-based index values to other CRT control parameters. For example, using an optimal AV delay setting, EGM-based index values can be obtained during pacing using an optimal VV delay (identified from surface ECG signal analysis) and multiple shifts from the optimal VV delay during atrial pacing and/or atrial sensing.

A look-up table of EGM-based index values for different AV and/or VV delay shifts may be established for multiple pacing vectors. For example different LV pacing vectors may be selected when a multipolar coronary sinus lead is used. A look-up table 400 may be stored in memory for each available pacing vector or a preferred subset of available pacing vectors.

Figure 5:
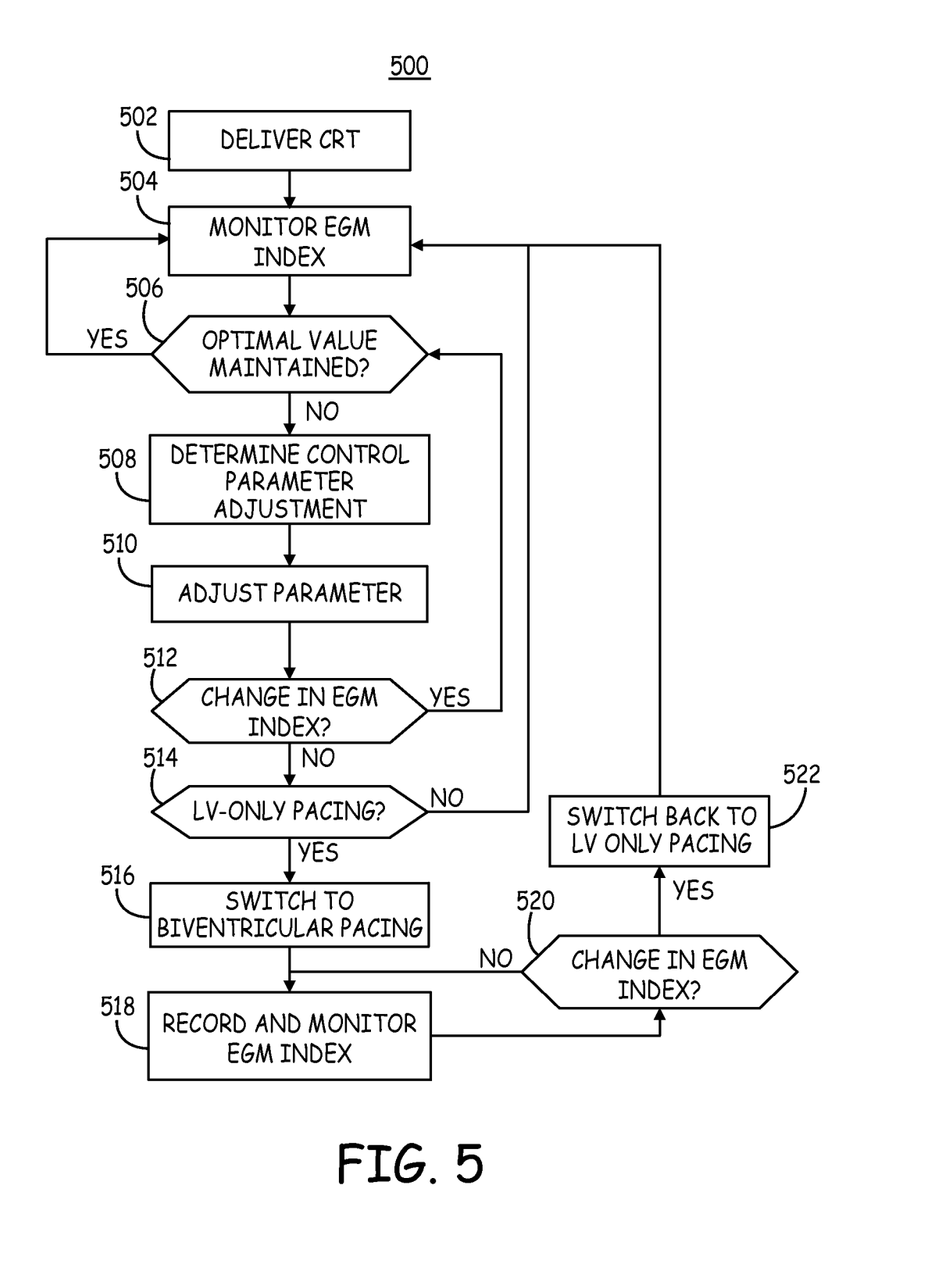
FIG. 5 is a flow chart of a method for controlling CRT control parameters in a closed-loop manner using an EGM-based index.

FIG. 5 is a flow chart 500 of a method for controlling CRT control parameters in a closed-loop manner using EGM-based index data. After establishing one or more look up tables in IMD memory 82, processor 80 uses the look up table data for controlling signal generator 84 to adjust a CRT parameter in response to determinations of the EGM-based ventricular dyssynchrony index made during CRT delivery. In the illustrative example, the CRT parameter being adjusted is AV delay, however, VV delay could be controlled in a closed loop manner based on look up table data and EGM-based index determinations made during CRT in a similar manner.

At block 502, CRT is delivered using an optimal parameter setting, e.g. AV delay for the current rhythm state (atrial sensing or pacing and LV-only or biventricular pacing) and currently selected pacing vector. The EGM-based index of ventricular dyssynchrony is monitored during CRT delivery at block 504. For example, sensing module 86 may provide cardiac signal analyzer 90 EGM signal data on every ventricular-paced cardiac cycle to enable continuous monitoring of the ventricular dyssynchrony index. Alternatively, the EGM-based index may be determined every Nth paced beat, at regular time intervals or according to any desired monitoring schedule. In some embodiments, the EGM-based index is at least determined each time a change in a CRT pacing occurs, including changes in atrial rate. For example, if the rhythm changes from a sensed atrial rhythm to a paced atrial rhythm or vice versa, if the rhythm changes between biventricular pacing and single ventricle pacing, if the heart rate changes, or if a pacing vector changes, the ventricular synchrony condition or state is monitored by determining an index from the EGM signal to determine if an adjustment to the AV delay is needed.

At block 506, the value of the EGM-based index determined during CRT delivery is looked up in a table 400 for the current rhythm state (e.g. SAV-BV, PAV-LV, SAV-BV, or PAV-BV) and stored for the selected pacing vector. If the index is approximately equal to the optimal value stored for a 0 ms AV delay shift, the AV delay remains unchanged and monitoring continues at block 504. If the EGM-based index has changed from the optimal value, indicating a change in ventricular dyssynchrony, an AV delay adjustment is determined at block 508. The AV delay adjustment is determined from the look up table 400 by looking up the EGM-based index value in the relevant portion of table 400 for the current rhythm state 402 and selected pacing vector. The AV delay adjustment is determined as the same magnitude but opposite polarity or direction of the AV delay shift associated with the current value of the EGM-based dyssynchrony index.

For example, in reference to look up table 400 of FIG. 4, if the current rhythm is SAV-BV 402A, and the EGM-based index is determined as being 34 ms, the associated AV delay shift is +30 ms. Since this value of the EGM-based index occurred for an AV delay that was shifted +30 ms from the optimal AV delay setting, the AV delay adjustment required to improve ventricular synchrony is −30 ms. By adjusting the current AV delay setting by −30 ms, the EGM-based index is expected to return to approximately 50 ms, corresponding to optimally synchronized electrical activation of the ventricles.

In some cases, an EGM-based index value 406 may be associated with more than one AV delay shift 404 for a given rhythm 402. For example, in look up table 400, the EGM-based dyssynchrony index is 80 ms for an AV delay shift of −40 ms and −50 ms during an SAV-BV rhythm 402a. In this case, the smaller adjustment may be selected first. For example, the AV delay may be adjusted by +40 ms in response to a determination of the EGM-based dyssynchrony index being 80 ms. Continued monitoring of the EGM-based dyssynchrony index will result in one or more additional adjustments of the AV delay if the first adjustment does not restore the EGM-based index to its optimal value, e.g. 50 ms in the illustrative example. The AV delay is adjusted at block 510 by the adjustment determined at block 508.

If a change in the EGM-based index is detected at block 512 in response to the adjusted parameter, CRT delivery may continue using the adjusted control parameter. The EGM-based index continues to be monitored at block 504 and readjustments to the control parameter are made as needed.

In some cases, the EGM-based index may not change in response to multiple adjustments to a control parameter. In such cases, intrinsic AV conduction block may be detected. In response to no change in the EGM-based index (block 512) following an adjustment of an AV delay, the processor and control 80 may control the signal generator 84 to alter the pacing therapy, e.g. by switching a pacing mode, because of the loss of intrinsic AV conduction. For example, AV block may be detected as evidenced by an EGM-based index value that remains substantially unchanged in response to a threshold number of adjustments to AV delay, e.g. three or more adjustments. If LV-only pacing is being delivered, as determined at block 514, the signal generator 84 may be switched to a biventricular pacing mode at block 516. Biventricular pacing may be delivered at a nominal AV delay setting since the EGM-based index is unresponsive to changes in AV delay. The nominal value of AV delay may range from 80 to 200 ms for sensed A-V delay and 120 to 250 ms for paced AV delay. In another embodiment, the IMD may deliver biventricular pacing at the optimal AV delay that was determined initially. In yet another embodiment the device may deliver pacing at a nominal AV delay without switching pacing mode.

The processor 80 may record and store the corresponding value of the EGM-based index at the onset of biventricular pacing (or nominal AV delay pacing without switching pacing mode) at block 518. Processor 80 continues to monitor the EGM-based index for any changes in the EGM index value.

If a change in the EGM-based index is detected during subsequent monitoring at block 520, (indicating a possible return of intrinsic AV conduction), the processor 80 may control the signal generator 84 to switch back to LV-only pacing at block 522 (if a pacing mode switch to biventricular pacing had been made previously). The EGM-based index is monitored again relative to its optimal value at blocks 504 and 506. Control parameter adjustments continue as needed to restore and maintain the EGM-based index at the established value corresponding to optimal electrical activation.

Using the disclosed techniques, a value for an EGM-based index that corresponds to a known state of optimal ventricular electrical synchrony, as initially determined by ECG-based surface potential analysis, is established for one or more rhythm states and/or one or more pacing vectors. Values of the index associated with non-optimized control parameter setting shifts, resulting in various states of ventricular dyssynchrony, are also established. This enables adjustments to a control parameter to be determined when deviations occur in the value of the EGM-based index from its established value at an optimal control parameter setting. An EGM-based index that deviates from the optimal value during a given rhythm state can be corrected and restored by adjusting a CRT timing control parameter based on an established relationship between the EGM-based index and control parameter shifts. This relationship may be stored in the form of a look up table as shown in FIG. 4 or in the form of a best fit equation to the data. An adjustment to a CRT control parameter is determined in response to a change in the EGM-based index by computing a shift from a best fit equation or looking up the associated shift in a look up table. The timing control parameter adjustment is the same magnitude but opposite polarity of the shift relative to the optimal setting.

Figure 6A:
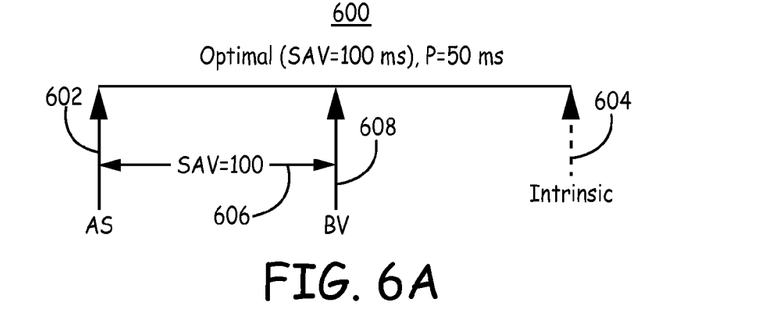
FIGS. 6A through 6D are a timing diagrams illustrating closed-loop control of an AV delay based on an EGM-based index.

FIGS. 6A through 6D are timing diagrams illustrating closed-loop control of the AV delay based on an EGM-based index. In FIG. 6A, timing diagram 600 shows the timing of an intrinsic atrial sense event 602 followed by the time of an expected intrinsic ventricular sense event 604. An optimal AV delay 606 for delivering biventricular pacing pulses 608 during atrial sensing (SAV) is identified as 100 ms based on analysis of activation times determined from surface ECG signals. This optimal SAV delay 606 may be established during a resting heart rate. For this optimal SAV delay 606, the EGM-based index P is determined to be 50 ms, which may be a time interval determined between a maximum and minimum peak amplitude of the EGM signal following a pacing pulse. This determination establishes the expected value of the EGM-based index when the ventricular activation is known to be in an optimized state of synchrony based on surface ECG activation times.

Figure 6B:
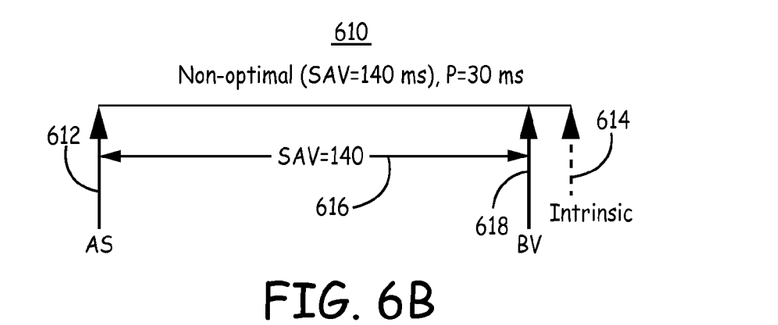

FIG. 6B shows a timing diagram 610 for one example of a non-optimal SAV delay 616 applied during the same resting heart rate and biventricular pacing conditions as timing diagram 600. The SAV delay has been increased to 140 ms, a shift of +40 ms relative to the optimal SAV delay. Biventricular pacing pulses 618 are delivered after the shifted SAV delay 616 following a sense atrial event 612. As can be seen, the biventricular pacing pulses are delivered just prior to an expected (but unknown) time of an intrinsic ventricular depolarization.

The EGM-based index (P) determined at this shifted SAV delay 616 is 30 ms. Thus, in a look up table, an EGM-based index value of 30 ms is stored for an SAV-BV rhythm and delay shift of +40 ms.

Figure 6C:
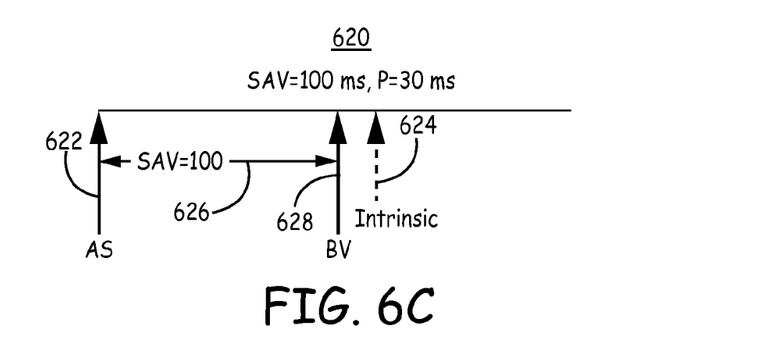

FIG. 6C is a timing diagram 620 during an increased heart rate, for example during exercise. The intrinsic ventricular depolarization 624 would occur at a shorter intrinsic AV interval after the atrial sense event 622. However, the timing of the intrinsic ventricular depolarization 624 is unknown since the ventricles are being paced by biventricular pacing pulses 628. Without having to detect a change in heart rate or a change in the intrinsic AV interval, the IMD processor 80 can adjust the SAV-BV delay 626 automatically by determining the EGM-based index (P) of ventricular dyssynchrony. For the higher heart rate condition shown in FIG. 7C, the SAV delay of 100 ms, which was optimal at a resting heart rate, results in an EGM-based index of ventricular dyssynchrony equal to 30 ms. This change in the EGM-based index from the optimal 50 ms to 30 ms indicates non-optimal ventricular electrical activation.

Figure 6D:
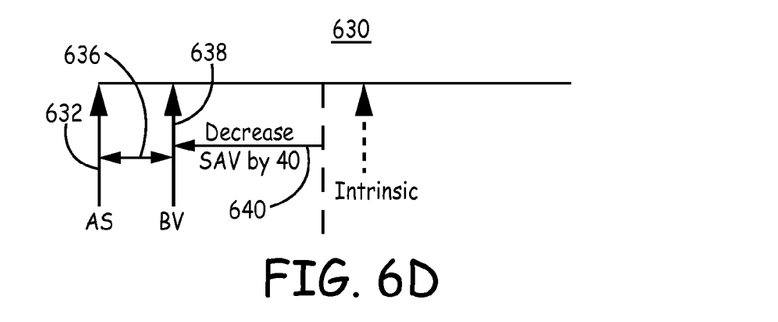

FIG. 6D is a timing diagram 630 illustrating a closed loop adjustment of the SAV delay. The EGM-based index value of 30 ms determined during the SAV-BV rhythm shown in FIG. 6C corresponds to an SAV delay shift of +40 ms based on the previously obtained data shown in FIG. 6B and stored in the form of a look up table in IMD memory 82. For this EGM-based index value, an AV delay adjustment 640 of −40 ms (same magnitude but opposite polarity of the SAV delay shift in FIG. 6B) is indicated. In order to restore the EGM-based index to its optimal value of 50 ms, or as close as possible to the optimal value, the SAV delay 636 is adjusted by −40 ms, to 60 ms. The EGM-based index may be re-determined to verify that it has returned to a value of approximately 50 ms. A relative increment or decrement of the AV delay that is needed to restore an optimal EGM-based index value is ascertained from the look up table and can be applied regardless of the actual AV delay setting at the time of the deviated, non-optimal EGM-based index determination.

The relationship between the EGM-based index and ventricular electrical dyssynchrony as a CRT control parameter changes is established by determining the EGM-based index for a known optimal ventricular activation condition and recording the index for multiple conditions shifted from the optimal ventricular activation condition. By establishing this relationship, determinations of the EGM-based index during CRT delivery enable closed loop adjustment of a CRT control parameter without additional sensors and without interrupting CRT therapy, for example to determine an intrinsic AV conduction time. In this way, CRT control parameters are adjusted to restore the EGM-based index to a value known to correspond to an optimal electrical activation state, i.e. optimal ventricular electrical synchrony.

Thus, various embodiments of an IMD system and method for closed loop adjustment of a CRT control parameter have been described. However, one of ordinary skill in the art will appreciate that various modifications may be made to the described embodiments without departing from the scope of the claims. For example, although specific examples of indices of ventricular dyssynchrony determined from surface ECG activation time and from an EGM signal, other indices or determinations of ventricular dyssynchrony may be determined from ECG and EGM signals according the techniques of this disclosure. Furthermore, although an EGM-based index has been described herein, it is recognized that an index may be determined from other cardiac signals and corresponding index data may be determined in the manner described herein for establishing a relationship between the index and an optimal ventricular synchrony condition and multiple non-optimal states. Adjustments to pacing therapy control parameters may be made to maintain the index at or near an established optimal value. These and other examples are within the scope of the following claims.

The invention claimed is:

1. A method for optimizing a pacing control parameter, comprising:
    determining a value of an EGM-based index corresponding to an optimal electrical activation condition of a patient's heart;
    delivering a pacing therapy to the heart;
    monitoring the EGM-based index during delivery of the pacing therapy to the heart; and
    adjusting the pacing therapy to maintain the EGM-based index at the value corresponding to the optimal electrical activation condition in response to detection of a value of the EGM-based index corresponding to a non-optimal electrical activation condition during the monitoring of the EGM-based index.

2. The method of claim 1, further comprising:
    establishing a relationship between the EGM-based index and a plurality of settings of a pacing control parameter, wherein establishing the relationship comprises:
        delivering cardiac pacing according to each of the plurality of settings comprising a previously established optimal setting and at least one non-optimal setting different than the optimal setting by a setting shift;
        determining a value of the EGM-based index from an EGM signal acquired during cardiac pacing at each of the plurality of settings; and
        storing the values of the determined index with corresponding setting shifts of each of the plurality of settings relative to the optimal setting; and
    enabling a processor of an implantable medical device to:
        monitor the EGM-based index during cardiac pacing, responsive to detecting an EGM-based index value corresponding to a non-optimal setting of the control parameter, determine an adjustment of the control parameter from the stored index values and corresponding setting shifts, and adjust the control parameter by the determined adjustment.

3. The method of claim 2, further comprising establishing the optimal setting by sensing surface potentials from a plurality of surface electrodes positioned on a patient's body and computing an index of ventricular dyssynchrony for each of a plurality of pacing control parameter settings in response to the sensed surface potentials.

4. The method of claim 2, wherein acquiring the EGM signal comprises selecting a sensing vector comprising a left ventricular electrode and a right ventricular coil electrode.

5. The method of claim 2, further comprising determining a magnitude and polarity of a setting shift corresponding to the detected EGM-based index corresponding to a non-optimal setting; and determining the adjustment as the magnitude and a polarity opposite to the setting shift corresponding to the detected EGM-based index.

6. The method of claim 2, wherein establishing the optimal pacing control parameter comprises establishing an optimal atrio-ventricular (AV) delay during cardiac resynchronization therapy.

7. The method of claim 2, further comprising establishing an optimal pacing control parameter and relationship between the EGM-based index and a plurality of settings of the control parameter for each of a plurality of different heart rhythm states.

8. The method of claim 2, further comprising establishing an optimal pacing control parameter and a relationship between the EGM-based index and a plurality of settings of the control parameter for each of a plurality of pacing electrode vectors.

9. The method of claim 2, further comprising storing the relationship as a look-up table of determined EGM-based index values and associated setting shifts in a memory of an implantable medical device accessed by the processor.

10. The method of claim 2, further comprising:

detecting an unchanged value of the EGM-based index in response to an adjustment of the control parameter; and switching a pacing mode in response to the unchanged value.

11. The method of claim 1, wherein determining the EGM-based index comprises detecting a maximum peak amplitude of the EGM signal following a pacing pulse.

12. The method of claim 1, wherein determining the EGM-based index comprises determining a time interval between a maximum peak amplitude and a minimum peak amplitude of the EGM signal following a pacing pulse.

13. A non-transitory, computer-readable storage medium comprising instructions that, when executed, cause a processor included in a medical device system to:

determine a value of an EGM-based index corresponding an optimal electrical activation condition of a patient's heart;

control a signal generator to deliver a pacing therapy to the heart;

monitor the EGM-based index during delivery of the pacing therapy to the heart; and adjust a pacing therapy control parameter to maintain the EGM-based index value corresponding to the optimal electrical activation condition in response to detection of a value of the EGM-based index corresponding to a non-optimal electrical activation condition during the monitoring of the EGM-based index.

14. The computer-readable storage medium of claim 13 further comprising instructions that, when executed, cause the processor to:

establish a relationship between an EGM-based index and a plurality of settings of a pacing control parameter, wherein establishing the relationship comprises:

delivering cardiac pacing pulses according to each of the plurality of settings comprising a previously established optimal setting and at least one non-optimal setting different than the optimal setting by a setting shift;

determining a value of the EGM-based index from the EGM signal acquired during cardiac pacing at each of the plurality of settings; and storing the values of the determined index with corresponding setting shifts of each of the plurality of settings relative to the optimal setting;

monitor the EGM-based index during cardiac pacing;

responsive to detecting an EGM-based index value corresponding to a non-optimal setting of the control parameter, determine an adjustment of the control parameter from the stored index values and corresponding setting shifts; and adjust the control parameter by the determined adjustment.

* * * * *